US010080496B2

(12) United States Patent
Tokuda et al.

(10) Patent No.: US 10,080,496 B2
(45) Date of Patent: Sep. 25, 2018

(54) OPHTHALMOLOGICAL DEVICE

(71) Applicant: TOPCON CORPORATION, Tokyo (JP)

(72) Inventors: Kanichi Tokuda, Tokyo (JP); Ryota Ishiai, Tokyo (JP)

(73) Assignee: Topcon Corporation (JP)

( * ) Notice: Subject to any disclaimer, the term of this patent is extended or adjusted under 35 U.S.C. 154(b) by 0 days.

(21) Appl. No.: 15/506,544

(22) PCT Filed: Aug. 18, 2015

(86) PCT No.: PCT/JP2015/073147
§ 371 (c)(1),
(2) Date: Feb. 24, 2017

(87) PCT Pub. No.: WO2016/031630
PCT Pub. Date: Mar. 3, 2016

(65) Prior Publication Data
US 2017/0251920 A1    Sep. 7, 2017

(30) Foreign Application Priority Data

Aug. 27, 2014  (JP) .................................. 2014-172695

(51) Int. Cl.
*A61B 3/14*    (2006.01)
*A61B 3/10*    (2006.01)
(Continued)

(52) U.S. Cl.
CPC ............ *A61B 3/152* (2013.01); *A61B 3/0025* (2013.01); *A61B 3/0058* (2013.01);
(Continued)

(58) Field of Classification Search
CPC ........... A61B 3/152; A61B 3/14; A61B 3/102; A61B 3/12; A61B 3/0025
(Continued)

(56) References Cited

U.S. PATENT DOCUMENTS 9,526,416 B2 *  12/2016  Fujimura ................. A61B 3/15
9,554,700 B2 *   1/2017  Nakahara ............... A61B 3/102
(Continued)

FOREIGN PATENT DOCUMENTS

JP    2007202724 A    8/2007
JP    2010181172 A    8/2010
(Continued)

OTHER PUBLICATIONS

International Search Report and Written Opinion dated Mar. 3, 2016, in connection with International Patent Application No. PCT/JP2015/073147, 7 pgs.
(Continued)

*Primary Examiner* — Mohammed Hasan
(74) *Attorney, Agent, or Firm* — Chiesa Shahinian & Giantomasi PC

(57) ABSTRACT

The ophthalmological device of an embodiment includes an optical system for inspection, a display, a subject's eye position acquiring unit, and a control unit. The optical system for inspection includes a photographic optical system for photographing an eyeground of the subject's eye. The subject's eye position acquiring unit acquires a three-dimensional position of the subject's eye. The control unit acquires information on positional displacement of the optical system for inspection with respect to the subject's eye on the basis of the three-dimensional position to cause a screen of the display to display two alignment index images to be varied in position with respect to a reference position of alignment preset in the display in a pseudo manner, in accordance with the information on positional displacement.

20 Claims, 10 Drawing Sheets

(51) Int. Cl.
    *A61B 3/15*     (2006.01)
    *A61B 3/00*     (2006.01)
    *A61B 3/117*     (2006.01)
    *A61B 3/12*     (2006.01)

(52) U.S. Cl.
    CPC ............ *A61B 3/0091* (2013.01); *A61B 3/102* (2013.01); *A61B 3/117* (2013.01); *A61B 3/1225* (2013.01); *A61B 3/154* (2013.01)

(58) Field of Classification Search
    USPC .................................................. 351/200–246
    See application file for complete search history.

(56) References Cited

U.S. PATENT DOCUMENTS 9,706,919 B2 * 7/2017 Ota .......................... A61B 3/14
9,848,767 B2 * 12/2017 Miyashita ............ A61B 3/0091
2011/0286003 A1 11/2011 Ono
2015/0085252 A1 3/2015 Fujimura et al.

FOREIGN PATENT DOCUMENTS

JP      2013248376 A      12/2013
JP      2014140542 A      8/2014

OTHER PUBLICATIONS

International Preliminary Report on Patentability dated Mar. 9, 2017, in connection with International Patent Application No. PCT/JP2015/073147, in Japanese (6 pgs.), with translation (7 pgs).
International Preliminary Report on Patentability dated Mar. 9, 2016, in connection with International Patent Application No. PCT/JP2015/073147, in Japanese (6 pgs.), with translation (7 pgs).
Notification of Reasons for Refusal dated Jul. 18, 2018, in connection with Japanese Patent Application No. 2014-172695, 6 pgs.

* cited by examiner

OPHTHALMOLOGICAL DEVICE

CROSS-REFERENCE TO RELATED APPLICATIONS

This application is a U.S. national phase filing under 35 U.S.C. § 371 of PCT Application No. PCT/JP2015/73147, filed Aug. 18, 2015, and claims priority thereto under 35 U.S.C. § 119 to Japanese Patent Application No. 2014-172695, filed Aug. 27, 2014, the entireties of both of which are incorporated by reference herein.

BACKGROUND OF THE INVENTION

Field of the Invention

The present invention relates to an ophthalmological device that optically inspects a subject's eye.

Description of the Related Art

An ophthalmological device includes an ophthalmological imaging device for acquiring an image of a subject's eye, and an ophthalmological measuring device for measuring characteristics of the subject's eye.

For example, the ophthalmological imaging device includes: an optical coherence tomograph that acquires a tomographic image by using optical coherence tomography (OCT); a fundus camera for photographing an eyeground; a scanning laser ophthalmoscope (SLO) that acquires an image of an eyeground by using laser scanning with a confocal optical system; and a slit lamp that acquires an image by using slit light to cut off an optical section of a cornea.

In addition, for example, the ophthalmological measuring device includes: an inspection device for refraction of eye (a refraction meter, or a keratometer) that measures refraction characteristics of a subject's eye; a tonometer; s specular microscope that acquires characteristics of a cornea (e.g. cornea thickness, and cell distribution); and a wavefront analyzer that acquires aberration information on a subject's eye by using a Hartmann-Shack sensor.

In an ophthalmological inspection using these devices above, from a viewpoint of accuracy and correctness of an inspection, positioning between an optical system for inspection (optical system of a device) and a subject's eye is very important. This positioning is called alignment. The alignment includes operation of aligning an optical axis of the optical system for inspection with an axis of the subject's eye (xy-alignment), and operation of adjusting a distance between the subject's eye and the optical system for inspection (z-alignment).

There is known a conventional ophthalmological device including an alignment optical system that projects an alignment index (luminous point alignment) for alignment of an optical system for inspection with respect to a subject's eye on the subject's eye (refer to Japanese Patent Application Laid-Open No. 2010-181172; hereinafter referred to as PTL 1, for example). In this ophthalmological device, while an observation image of a subject's eye displayed in a monitor is observed, alignment of the optical system for inspection with respect to a subject's eye is performed by operating a control lever to three-dimensionally move the optical system for inspection such that two alignment index images enter the inside of an alignment reference position mark (an alignment scale).

SUMMARY OF THE INVENTION

In the conventional ophthalmological device, when a central portion of an eyeground is photographed, photographing is performed while a fixation target is projected toward a subject's eye from a direction along an optical axis of the optical system for inspection so that a line of sight of the subject's eye is aligned with the optical axis of the optical system for inspection. Meanwhile, when a peripheral portion of the eyeground is photographed, photographing is performed while the fixation target is projected from a direction different from the optical axis of the optical system for inspection so that the line of sight of the subject's eye is pointed to the direction different from the optical axis of the optical system for inspection. At this time, while a tip of a cornea and a center of a pupil coincide with each other when the central portion of the eyeground is photographed, the tip of the cornea and the center of the pupil are displaced from each other when the peripheral portion of the eyeground is photographed. In this case, aligning the optical axis with the tip of the cornea may cause illumination light for the eyeground to be blocked by an iris. Thus, when the peripheral portion of the eyeground is photographed, an alignment reference position is changed so that the optical axis is aligned with a portion near the center of the pupil.

Unfortunately, in this kind of conventional ophthalmological device, if positional displacement of an optical system for inspection with respect to subject's eye is large, one or two alignment index images may sometimes disappear from a screen of a monitor. In particular, when a peripheral portion of an eyeground is photographed, photographing is performed while a line of sight of a subject's eye is pointed to a direction different from an optical axis of an optical system for inspection as described above. As a result, as an alignment reference position changes, an alignment index image projected in a peripheral portion of a cornea tends to easily disappear from the screen of the monitor. Since this kind of case is difficult for a person unskilled in operation to understand, even improper alignment of the optical system for inspection with respect to the subject's eye may be misidentified as proper alignment. In addition, an operator needs to move the optical system for inspection until two alignment index images appear in the screen of the monitor while repeating trial and error on the basis of experience and intuition of the operator, and thus this causes adjustment of alignment to take time.

In recent years, while a device is required to be reduced in size and cost, it is desired to develop an ophthalmological device capable of easily performing alignment adjustment by hand (manual alignment) with a familiar operational feeling without mounting an alignment optical system.

The present invention is made in light of the above-mentioned circumstances, and an object thereof is to provide an ophthalmological device capable of smoothly and easily performing alignment of an optical system for inspection with respect to a subject's eye by hand with a familiar operational feeling without increasing cost and size of the device.

To achieve the object described above, an ophthalmological device according to a first aspect of the present invention includes: an optical system for inspection including a photographic optical system for photographing an eyeground of a subject's eye; a display that displays an eyeground image of the subject's eye acquired by the photographic optical system; a subject's eye position acquiring unit that acquires a three-dimensional position of the subject's eye; and a control unit that acquires information on positional displacement of the optical system for inspection with respect to the subject's eye on the basis of the three-dimensional position to cause a screen of the display to display two alignment index images to be varied in position with respect to a reference position of alignment preset in the display in a pseudo manner, in accordance with the information on positional displacement.

In the first aspect, an ophthalmological device according to a second aspect of the present invention includes the control unit that causes the two alignment index images to be displayed at the reference position of alignment when the optical system for inspection is at a proper position with respect to the subject's eye.

In the first or second aspect, an ophthalmological device according to a third aspect of the present invention includes the information on positional displacement that includes an amount of positional displacement and a positional displacement direction in an optical axis direction of the optical system for inspection, and the control unit changes a distance between the two alignment index image in accordance with the amount of positional displacement as well as changes a display mode of the two alignment index images in accordance with the positional displacement direction.

In the third aspect, an ophthalmological device according to a fourth aspect of the present invention includes the control unit that changes at least one display mode among color, shape, size, blinking pattern, pattern, brightness, density, and transparency, of the two alignment index images, in accordance with the positional displacement direction.

In any one of the first to fourth aspects, an ophthalmological device according to a fifth aspect of the present invention further includes a fixation optical system for fixing the subject's eye, wherein the control units causes an alignment reference position mark to be always displayed at a predetermined reference position regardless of change in a fixation position of the subject's eye by the fixation optical system.

In any one of the first to fifth aspects, an ophthalmological device in accordance with a sixth aspect of the present invention includes the subject's eye position acquiring unit that includes two or more photographing units each of which substantially simultaneously photographs an anterior eye of the subject's eye from a different direction, and an analysis unit that analyzes photographed images acquired by the two or more photographing units to acquire a three-dimensional position of the subject's eye.

According to the present invention, it is possible to smoothly and easily perform alignment of an optical system for inspection with respect to a subject's eye by hand with a familiar operational feeling without increasing cost and size of the device.

DETAILED DESCRIPTION OF THE EXEMPLARY EMBODIMENTS

An example of an embodiment of an ophthalmological device according to the present invention will be described in detail with reference to accompanying drawings. The ophthalmological device according to the present invention is used for an optical inspection of a subject's eye. This kind of ophthalmological device includes an ophthalmological imaging device, and an ophthalmological measuring device, as described above. The ophthalmological imaging device includes an optical coherence tomograph, a fundus camera, a scanning laser ophthalmoscope, a slit lamp, and the like. The ophthalmological measuring device includes an inspection device for refraction of eye, a tonometer, a specular microscope, a wavefront analyzer, and the like. While a case of applying the present invention to an optical coherence tomograph will be described in detail in the embodiment below, the present invention can be applied to any ophthalmological device other than that.

In the present specification, an image acquired by an OCT may be sometimes collectively called an OCT image. In addition, measurement operation to form the OCT image may be sometimes called OCT measurement. Contents of a document described in the present specification can be appropriately quoted as contents of the embodiment below.

While an optical coherence tomograph using an OCT provided with a low coherence light source and a spectroscope, so-called a spectral domain type, will be described in the embodiment below, the present invention can be applied to an optical coherence tomograph using OCT means of a type other than the spectral domain type, such as a swept source type, and an en-face type. The swept source OCT is means for performing imaging of a form of an object to be measured as follows: wavelengths of light emitted to an object to be measured (wavelength sweep) are scanned; an interfering light acquired by superimposing a reflected light of each of lights with the respective wavelengths and a reference light is detected to acquire spectra intensity distribution; and Fourier transform is applied to the spectra intensity distribution. The en-face OCT is means for forming an image of the object to be measured in a section orthogonal to a direction of travel of light as follows: an object to be measured is irradiated with the light with a predetermined beam diameter; and components of an interfering light acquired by superimposing a reflected light of the irradiated light and a reference light are analyzed, and the en-face OCT means is also called a full-field type.

While a device configured by combining an OCT device and a fundus camera is described in the embodiment below, an application item of the present invention is not limited to a complex machine such as described above, and the present invention also can be applied to an ophthalmological device as a single machine (e.g. a fundus camera alone).

(Configuration)

Figure 1:
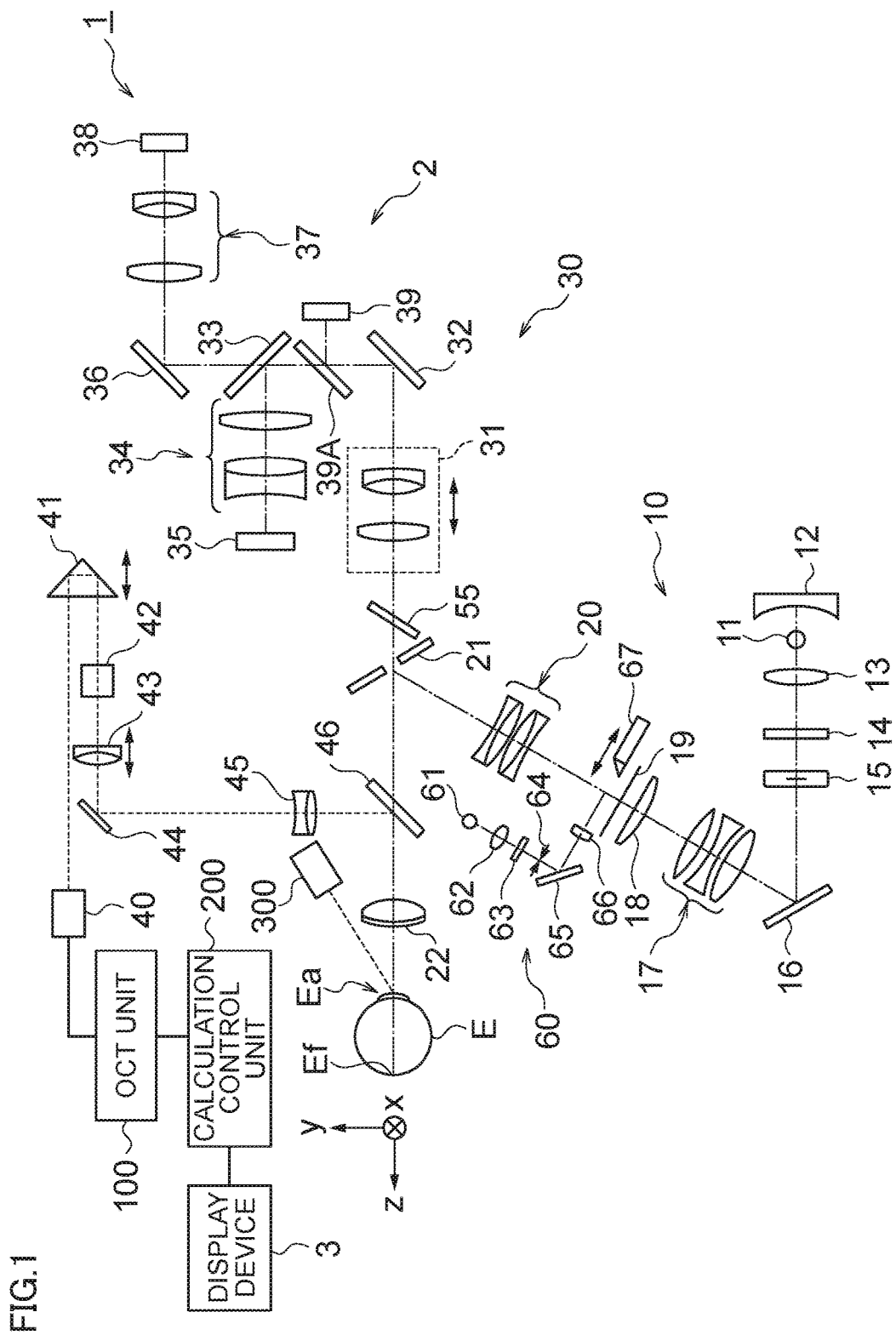
FIG. 1 is a schematic view illustrating an example of a general configuration of an embodiment of an ophthalmological device according to the present invention.

As illustrated in FIG. 1, an ophthalmological device 1 includes a fundus camera unit 2, an OCT unit 100, and a calculation control unit 200. The fundus camera unit 2 has an optical system that is almost the same as that of a conventional fundus camera. The OCT unit 100 is provided with an optical system for acquiring an OCT image of an eyeground. The calculation control unit 200 includes a computer that executes various calculation processes, control processes, and the like.

(Fundus Camera Unit)

The fundus camera unit 2 illustrated in FIG. 1 is provided with an optical system for acquiring a two-dimensional image (eyeground image) showing a surface form of an eyeground Ef of a subject's eye E. The eyeground image includes images such as an observation image and a photographed image. The observation image is a monochrome dynamic image formed by using far-red light at a predetermined frame rate, for example. When the optical system is focused on an anterior eye Ea of the subject's eye E, the fundus camera unit 2 is able to acquire an observation image of the anterior eye Ea. The photographed image, for example, may be a color image acquired by flashing visible light, or a monochrome still image acquired by using far-red light or visible light as illumination light. The fundus camera unit 2 is may be configured to be able to acquire images other than the above, such as a fluorescein fluorescent image, an indocyanine green fluorescent image, and a spontaneous emission fluorescent image.

Figure 4A:
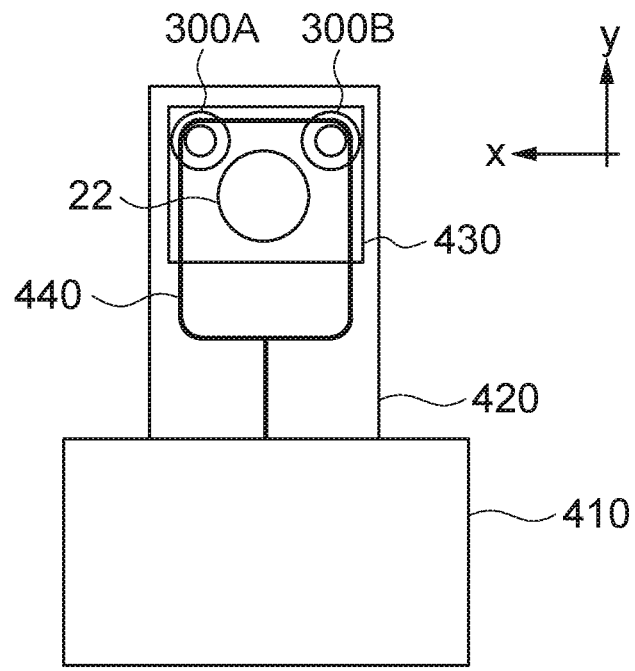
FIG. 4A is a schematic view illustrating an example of an appearance configuration of the embodiment of the ophthalmological device according to the present invention.
Figure 4B:
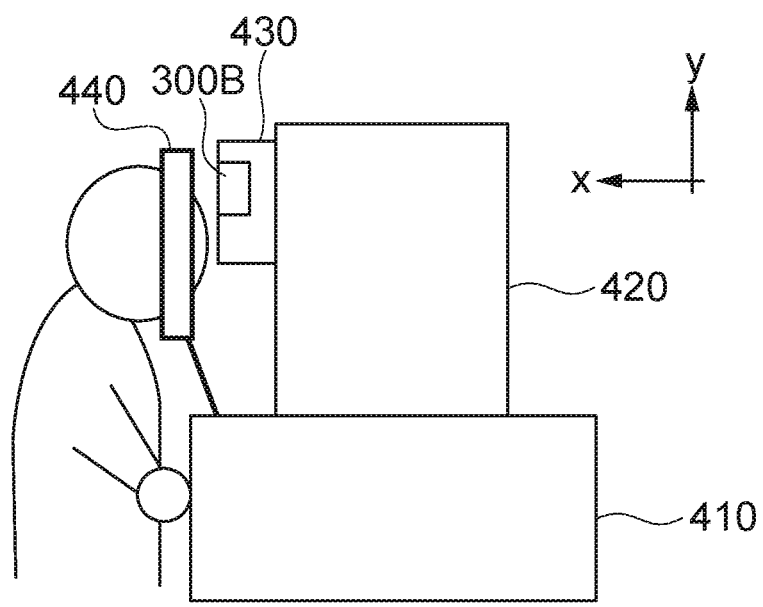
FIG. 4B is a schematic view illustrating an example of an appearance configuration of the embodiment of the ophthalmological device according to the present invention.

The fundus camera unit 2 is provided with a chin mount and a forehead pad to support a face of a subject. The chin mount and the forehead pad correspond to a support part 440 illustrated in FIGS. 4A and 4B. In FIGS. 4A and 4B, a reference numeral 410 designates a base that stores a driving system, such as an optical system driving unit 2A, and a calculation control circuit. A reference numeral 420 designates a body that is provided on the base 410 and stores an optical system. In addition, a reference numeral 430 designates a lens accommodation unit that is provided so as to project from a front face of the body 420 and stores an objective lens 22.

The fundus camera unit 2 is provided with an illumination optical system 10 and a photographic optical system 30. The illumination optical system 10 emits illumination light to the eyeground Ef. The photographic optical system 30 guides a light reflected by the eyeground in the illumination light to imaging devices (CCD image sensors 35 and 38, or the CCD image sensors may be simply called CCDs). In addition, the photographic optical system 30 guides signal light from the OCT unit 100 to the eyeground Ef as well as the signal light passing through the eyeground Ef to the OCT unit 100.

An observation light source 11 of the illumination optical system 10 is composed of a halogen lamp, for example. Light outputted from the observation light source 11 (observation illumination light) is reflected by a reflection mirror 12 with a curved reflection surface, and passes through a visible light cut filter 14 through a condenser lens 13 to be transferred to far-red light. In addition, the observation illumination light temporarily converges at a portion near a photographing light source 15 to be reflected by a mirror 16, and passes through relay lenses 17 and 18, a diaphragm 19, and a relay lens 20. Then the observation illumination light is reflected by a peripheral portion of a mirror with an aperture 21 (an area of a periphery of the aperture), and passes through a dichroic mirror 46 to be refracted by the objective lens 22 to illuminate the eyeground Ef. For the observation light source, a light emitting diode (LED) is also available.

Light reflected by the eyeground in the observation illumination light is refracted by the objective lens 22, and passes through the dichroic mirror 46, an aperture formed in a center area of the mirror with an aperture 21, and a dichroic mirror 55 to be reflected by a mirror 32 through a focal lens 31. In addition, the light reflected by the eyeground passes through a half mirror 39A to be reflected by a dichroic mirror 33, and then an image is formed in a receiving surface of a CCD image sensor 35 by the light reflected passed through a condenser lens 34. The CCD image sensor 35 detects the light reflected by the eyeground at a predetermined frame rate, for example. A display device 3 displays an image (observation image) based on the light reflected by the eyeground detected by the CCD image sensor 35. When the photographic optical system is focused on the anterior eye, an observation image of the anterior eye of the subject's eye E is displayed.

The photographing light source 15 is composed of a xenon lamp, for example. Light (photographing illumination light) outputted from the photographing light source 15 passes through a path similar to that of the observation illumination light to be emitted to the eyeground Ef. The light reflected by the eyeground of the photographing illumination light passes through a path similar to that of the observation illumination light to be guided to the dichroic mirror 33, and passes through the dichroic mirror 33 to be reflected by a mirror 36, and then an image is formed in a receiving surface of a CCD image sensor 38 by the light reflected passed through a condenser lens 37. The display device 3 displays the image (photographed image) based on the light reflected by the eyeground detected by the CCD image sensor 38. The display device 3 for displaying the observation image, and the display device 3 for displaying the photographed image, may be the same or different. When the subject's eye E is illuminated with infrared light to perform similar photographing, an infrared photographed image is displayed. In addition, an LED also can be used for the photographing light source.

A liquid crystal display (LCD) 39 displays a fixation target and an index of eyesight measurement. The fixation target is an index for vision fixation of the subject's eye E, and is used at the time of eyeground photographing, OCT measurement, or the like.

A part of light outputted from the LCD 39 is reflected by the half mirror 39A to be reflected by the mirror 32, and then passes through the aperture of the mirror with an aperture 21 through the focal lens 31 and the dichroic mirror 55 to be transmitted through the dichroic mirror 46, and subsequently is refracted by the objective lens 22 to be projected on the eyeground Ef.

Changing a display position of the fixation target in a screen of the LCD 39 enables changing a projection direction of the fixation target with respect to the subject's eye E, or a fixation position of the subject's eye E. For example, as with a conventional fundus camera, the fixation position of the subject's eye E includes positions, such as: a position for acquiring an image in which macula lutea of the eyeground Ef is centered; a position for acquiring an image in which an optic disk is centered; and a position for acquiring an image in which the center of the eyeground, positioned between the macula lutea and the optic disk, is centered. In addition, it is also possible to arbitrarily change the display position of the fixation target. A configuration for fixation to the subject's eye E corresponds to an example of a "fixation optical system".

Means for projecting a fixation target on the subject's eye E is not limited to the above. For example, a fixation position can be changed by providing a LED group formed by arranging a plurality of LEDs and selectively lighting the LEDs. In addition, a fixation position can also be changed by providing one or more movable LEDs.

The fundus camera unit 2 includes a focus optical system 60. The focus optical system 60 creates an index (split index) for focusing on the eyeground Ef.

When focus adjustment is performed, a reflection surface of a reflection bar 67 is provided at an angle in an optical path of the illumination optical system 10. Light (focus light) outputted from a LED 61 of the focus optical system 60 passes through a relay lens 62 to be split into two pencils of light by a split index plate 63, and passes through a two-aperture diaphragm 64, and then is reflected by a mirror 65 to temporarily form an image on a reflection surface of the reflection bar 67 through a condenser lens 66, and is reflected by the reflection surface. Then, the focus light is reflected by the mirror with an aperture 21 through the relay lens 20 to be transmitted through the dichroic mirror 46, and then is refracted by the objective lens 22 to be projected on the eyeground Ef.

Light reflected by the eyeground in the focus light passes through a path similar to that of light reflected by a cornea in alignment light to be detected by the CCD image sensor 35. A light-receiving image (split index) created by the CCD image sensor 35 is displayed in the display device 3 together with an observation image. The calculation control unit 200 analyzes a position of the split index to allow the focal lens 31 and the focus optical system 60 to move for focusing (autofocus function), as before. The focusing may be performed by hand while the split index is visually identified.

The dichroic mirror 46 causes an optical path for OCT measurement to branch from an optical path for eyeground photographing. The dichroic mirror 46 reflects light within a wavelength range to be used for the OCT measurement, and causes light for eyeground photographing to be transmitted therethrough. The optical path for OCT measurement includes a collimator lens unit 40, an optical path length changing unit 41, a galvanoscanner 42, a focal lens 43, a mirror 44, and a relay lens 45, in order from an OCT unit 100 side.

The optical path length changing unit 41 is movable in a direction of an arrow illustrated in FIG. 1 to change length of the optical path for OCT measurement. This change in length of the optical path is used for correction of length of the optical path in accordance with eye axial length of the subject's eye E, adjustment of conditions of interference, and the like. The optical path length changing unit 41 includes a corner cube, and a mechanism for moving the corner cube, for example.

The galvanoscanner 42 changes a direction of travel of light (signal light LS) passing through the optical path for OCT measurement. This enables the eyeground Ef to be scanned with the signal light LS. The galvanoscanner 42 includes a galvanomirror that causes the signal light LS to sweep in an x-direction, a galvanomirror that causes the signal light LS to sweep in a y-direction, and a mechanism for independently driving the galvanomirrors, for example. This enables the signal light LS to sweep in any direction in an xy-plane.

The fundus camera unit 2 includes an anterior eye camera 300. The anterior eye camera 300 substantially simultaneously photographs the anterior eye Ea from different directions. In this embodiment, the fundus camera unit 2 is provided in its face on a subject side with two cameras (refer to anterior eye cameras 300A and 300B illustrated in FIG. 4A). Each of the anterior eye cameras 300A and 300B is provided at a position away from the optical path of the illumination optical system 10 and an optical path of the photographic optical system 30, as illustrated in FIGS. 1 and 4A. Hereinafter, the two anterior eye cameras 300A and 300B may be collectively designated by a reference numeral 300.

While the two anterior eye cameras 300A and 300B are provided in this embodiment, the number of anterior eye cameras in the present invention is any number of two or more. However, in consideration of calculation processing described later, even configuration capable of substantially simultaneously photographing an anterior eye from two different directions is available. In addition, in this embodiment, while the illumination optical system 10 and the photographic optical system 30 are individually provided with the anterior eye camera 300, at least the photographic optical system 30 enables similar anterior eye photographing to be performed. Thus, a configuration in which one of two or more anterior eye cameras is provided in the photographic optical system 30 may be available. That is, this embodiment allows any configuration capable of substantially simultaneously photographing an anterior eye from two or more different directions.

The term, "substantially simultaneously", indicates that a deviation of photographing timing negligible compared with eye movement is allowed in photographing with two or more anterior eye cameras. This enables acquiring an image of the subject's eye E that is at substantially the same position (direction) with two or more anterior eye cameras.

While the photographing with two or more anterior eye cameras is available for taking a moving image and a still image, a case of taking a moving image will be particularly described in detail in this embodiment. In a case of taking a moving image, the substantially simultaneous photographing of an anterior eye described above can be achieved by controlling the following: timing of starting photographing so as to coincide with each other; a frame rate; and timing of photographing for each frame. Meanwhile, in a case of photographing of a still image, the photographing can be achieved by controlling timing of the photographing so as to coincide with each other.

This embodiment enables positioning (alignment) of an optical system for inspection with respect to the subject's eye E to be performed by using the two anterior eye cameras 300A and 300B, as described in detail later.

(OCT Unit)

Figure 2:
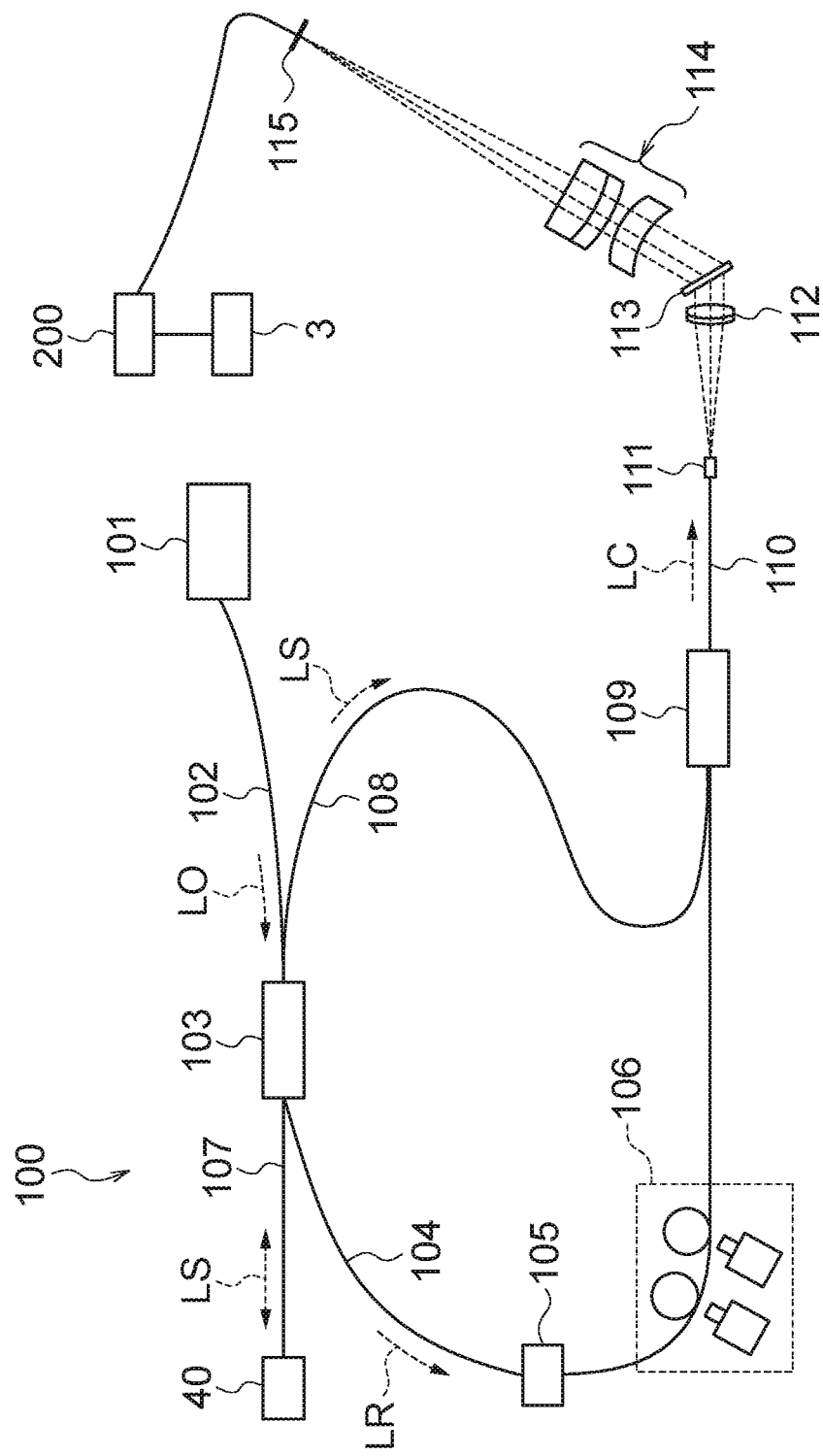
FIG. 2 is a schematic view illustrating an example of a configuration of an OCT unit in the embodiment of the ophthalmological device according to the present invention.

With reference to FIG. 2, an example of a configuration of the OCT unit 100 will be described. The OCT unit 100 is provided with an optical system for acquiring an OCT image of the eyeground Ef. The optical system has a configuration similar to that of an OCT device of a conventional spectral domain type. That is, the optical system is configured as follows: low coherence light is split into reference light and signal light; the signal light through the eyeground Ef and the reference light through a reference optical path are caused to interfere with each other to create interfering light; and spectra components of the interfering light is detected. This detection result (detection signal) is transmitted to the calculation control unit 200.

An OCT device of a swept source type includes a wavelength swept light source instead of a light source for outputting low coherence light, and no optical member for applying spectral resolution to interfering light. Generally, a well-known art corresponding to a type of an OCT can be appropriately applied to a configuration of the OCT unit 100.

The light source unit 101 outputs wide-band low coherence light L0. The low coherence light L0 includes a wavelength range in a far-red area (of the order of 800 nm to 900 nm), and has temporal coherence length of the order of a few tens micro meters, for example. A wavelength range invisible to a human eye, such as far-red light having a central wavelength of the order of 1040 nm to 1060 nm, may be used for the low coherence light L0.

The light source unit 101 includes an optical output device, such as a super luminescent diode (SLD), an LED, and a semiconductor optical amplifier (SOA).

The low coherence light L0 outputted from the light source unit 101 is guided to a fiber coupler 103 through an optical fiber 102 to be split into the signal light LS and reference light LR.

The reference light LR is guided through the optical fiber 104 to reach an optical attenuator 105. The optical attenuator 105 automatically adjusts an amount of reference light LR to be guided into the optical fiber 104 by using a well-known art under control of the calculation control unit 200. The reference light LR with an amount adjusted by the optical attenuator 105 is guided through the optical fiber 104 to reach a polarization regulator (polarization controller) 106. The polarization regulator 106 adjusts a polarization state of the reference light LR guided through the optical fiber 104 by applying stress to the optical fiber 104 formed into the shape of a loop from the outside, for example. A configuration of the polarization regulator 106 is not limited to the configuration described above, and thus any publicly known art can be used. The reference light LR with a polarization state adjusted by the polarization regulator 106 reaches a fiber coupler 109.

The signal light LS created by the fiber coupler 103 is guided through the optical fiber 107 to be formed into a parallel pencil by the collimator lens unit 40. In addition, the signal light LS reaches the dichroic mirror 46 through the optical path length changing unit 41, the galvanoscanner 42, the focal lens 43, the mirror 44, and the relay lens 45. Then the signal light LS is reflected by the dichroic mirror 46, and then is refracted by the objective lens 22 to illuminate the eyeground Ef. The signal light LS is scattered (including reflection) in various depth positions of the eyeground Ef. Backscattered light of the signal light LS scattered by the eyeground Ef inversely travels through the same path as that of incidence, and is guided through the fiber coupler 103 to reach the fiber coupler 109 through the optical fiber 108.

The fiber coupler 109 causes the backscattered light of the signal light LS and the reference light LR through the optical fiber 104 to interfere with each other. Interference light LC created by the fiber coupler 109 is guided through the optical fiber 110 to be emitted from an emission end 111. In addition, the interfering light LC is formed into a parallel pencil through a collimator lens 112 to be dispersed (spectral resolution) through a diffraction grating 113, and then is concentrated through a condenser lens 114 to be projected on a receiving surface of a CCD image sensor 115. While the diffraction grating 113 illustrated in FIG. 2 is a transmission type, a spectroscopic element of another type, such as a diffraction grating of a reflection type, can also be used.

The CCD image sensor 115 is a line sensor that detects each spectra component of the dispersed interfering light LC, and that converts it into electric charge, for example. The CCD image sensor 115 accumulates the electric charge to create a detection signal, and then transmits the signal to the calculation control unit 200.

While this embodiment uses a Michelson type interferometer, any type of interferometer, such as a Mach-Zehnder type, may be appropriately used. Instead of the CCD image sensor, an image sensor of another type, such as a complementary metal oxide semiconductor (CMOS) image sensor, can be used.

(Calculation Control Unit)

A configuration of the calculation control unit 200 will be described. The calculation control unit 200 analyzes a detection signal received from the CCD image sensor 115 to create an OCT image of the eyeground Ef. Calculation processing for that is the same as that of an OCT device of a conventional spectral domain type.

The calculation control unit 200 controls each of the fundus camera unit 2, the display device 3, and the OCT unit 100. For example, the calculation control unit 200 causes the display device 3 to display an OCT image of the eyeground Ef.

In addition, the calculation control unit 200 performs control of the fundus camera unit 2, such as: control of operation of the observation light source 11, the photographing light source 15, and the LED 61; control of operation of the LCD 39; control of movement of the focal lenses 31 and 43; control of movement of the reflection bar 67; control of movement of the focus optical system 60; control of movement of the optical path length changing unit 41; control of operation of the galvanoscanner 42; and control of operation of the anterior eye camera 300.

Further, the calculation control unit 200 performs control of the OCT unit 100, such as: control of operation of the light source unit 101; control of operation of the optical attenuator 105; control of operation of the polarization regulator 106; and control of operation of the CCD image sensor 115.

The calculation control unit 200, as with a conventional computer, includes a microprocessor, a RAM, a ROM, a hard disk drive, and a communication interface, for example. A storage device, such as a hard disk drive, stores a computer program for controlling an ophthalmological device 1. The calculation control unit 200 may include various circuit boards such as a circuit board for forming an OCT image. In addition, the calculation control unit 200 may include an operation device (input device) such as a keyboard and a mouse, and a display device such as a LCD.

The fundus camera unit 2, the display device 3, the OCT unit 100, and the calculation control unit 200, may be integrally formed (or formed in a single body), or may be separately formed in two or more bodies.

(Control System)

Figure 3:
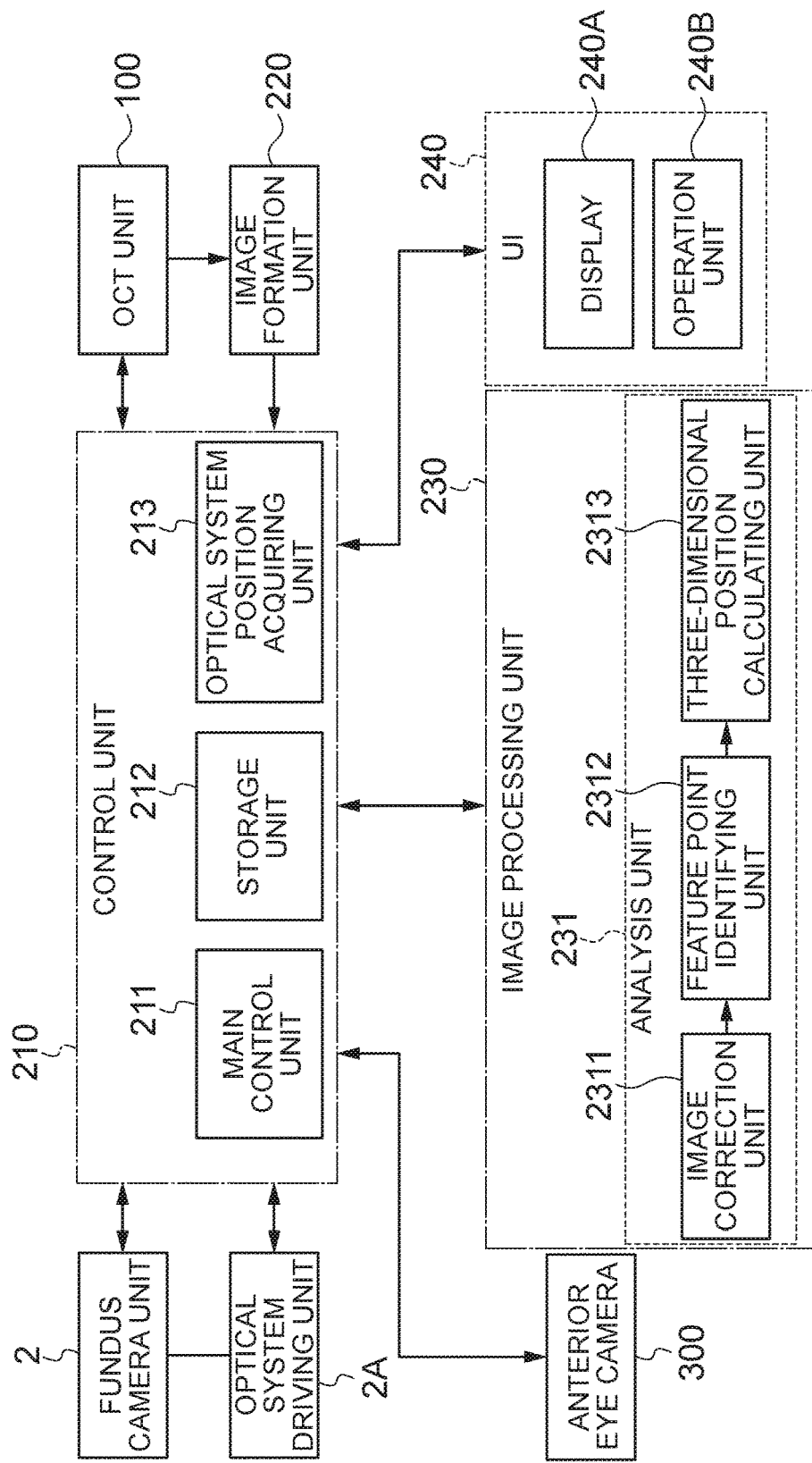
FIG. 3 is a schematic block diagram view illustrating an example of a configuration of a control system of the embodiment of the ophthalmological device according to the present invention.

A configuration of a control system of the ophthalmological device 1 will be described with reference to FIG. 3.

(Control Unit)

The control system of the ophthalmological device 1 is mainly composed of a control unit 210. The control unit 210 includes the microprocessor, the RAM, the ROM, the hard disk drive, and the communication interface, described above, for example. The control unit 210 is provided with a main control unit 211, a storage unit 212, and an optical system position acquiring unit 213.

(Main Control Unit)

The main control unit 211 performs the various control processes of operation described above. Control of movement of the focal lens 31 is performed by controlling a focal driving unit (not illustrated) to move the focal lens 31 in the optical axis direction. This changes an in-focus position of the photographic optical system 30. In addition, the main control unit 211 is capable of controlling the optical system driving unit 2A to move an optical system provided in the fundus camera unit 2 in a three-dimensional manner.

While the optical system driving unit 2A of this embodiment moves the optical system provided in the fundus camera unit 2, the optical system driving unit 2A may be configured so as to move the optical system provided in the fundus camera unit 2 and an optical system provided in the OCT unit 100.

Since the anterior eye camera 300 of this embodiment is provided in a body of the fundus camera unit 2, the anterior eye camera 300 can be moved by controlling the optical system driving unit 2A. It is possible to provide a photographing moving unit capable of independently moving each of two or more anterior eye cameras 300. Specifically, the photographing moving unit may include a drive mechanism (e.g. an actuator, and a power transmission mechanism) provided in each of the anterior eye cameras 300. In addition, the photographing moving unit may be configured so as to transmit power generated by a single actuator to a power transmission mechanism provided for each of the anterior eye cameras 300 to move the two or more anterior eye cameras 300.

The main control unit 211 performs processing of writing data into the storage unit 212, and processing of reading out data from the storage unit 212.

(Storage Unit)

The storage unit 212 stores various data items. The data stored in the storage unit 212 includes image data on an OCT image, image data on an eyeground image, and information on the subject's eye, for example. The information on a subject's eye includes information on a subject such as a patient ID and a name, and information on a subject's eye such as information on identification of left eye/right eye. In addition, the storage unit 212 stores various programs and data items for operating the ophthalmological device 1.

The storage unit 212 previously stores information on aberration (not illustrated). The information on aberration includes information on distortion aberration that occurs in a photographed image due to influence of an optical system provided in each of the anterior eye cameras 300. The optical system provided in the anterior eye camera 300 includes an optical element such as a lens that causes distortion aberration, for example. The information on aberration can be said as a parameter for quantifying distortion applied to a photographed image by these optical elements. A specific example of a method of creating the information on aberration is described in Japanese Patent Application Laid-Open No. 2013-248376 (hereinafter referred to as PTL 2) filed by the present applicant, for example.

(Optical System Position Acquiring Unit)

The optical system position acquiring unit 213 acquires a current position of the optical system for inspection provided in the ophthalmological device 1. The optical system for inspection is an optical system used to optically inspect a subject's eye E. The optical system for inspection in the ophthalmological device 1 (a complex machine of a fundus camera and an OCT device) of this embodiment is an optical system to acquire an image of a subject's eye, and thus includes the photographic optical system 30.

The optical system position acquiring unit 213 receives information showing contents of control of movement of the optical system driving unit 2A by the main control unit 211 to acquire a current position of the optical system for inspection moved by the optical system driving unit 2A, for example. A specific example of this processing will be described. The main control unit 211 controls the optical system driving unit 2A at predetermined timing (e.g. at the time of starting a device, and at the time of inputting information on a patient) to cause the optical system for inspection to move to a predetermined initial position. After that, the main control unit 211 records contents of control every time when the optical system driving unit 2A is controlled. This enables history of contents of control to be acquired. The optical system position acquiring unit 213 acquires contents of control up to the present with reference to the history to acquire a current position of the optical system for inspection on the basis of the contents of control.

In addition, every time when the main control unit 211 controls the optical system driving unit 2A, contents of control may be transmitted to the optical system position acquiring unit 213 so that the optical system position acquiring unit 213 sequentially acquires a current position of the optical system for inspection every time when receiving the contents of control.

As another example of a configuration, a position sensor for detecting a position of the optical system for inspection may be provided in the optical system position acquiring unit 213.

When the optical system position acquiring unit 213 acquires a current position of the optical system for inspection as described above, the main control unit 211 is able to acquire information on positional displacement of the optical system for inspection with respect to the subject's eye E on the basis of the acquired current position and a three-dimensional position of the subject's eye E acquired by an analysis unit 231 described below. Specifically, the main control unit 211 identifies the current position of the optical system for inspection by using a result acquired by the optical system position acquiring unit 213, as well as the three-dimensional position of the subject's eye E by using a result analyzed by the analysis unit 231. Next, the main control unit 211 acquires an amount and direction of the positional displacement from a proper position of the optical system for inspection with respect to the subject's eye E in each of the x-direction (side-to-side direction), the y-direction (vertical direction), and the z-direction (direction of working distance), on the basis of the current position of the optical system for inspection and the three-dimensional position identified by the analysis unit 231. Then, the main control unit 211 causes a pseudo alignment index image and an alignment reference position mark to be displayed at a predetermined position in a screen of a display 240A, while superimposing them on an observation image to form a composite display, in accordance with the acquired amount and direction of positional displacement in each of the directions. The alignment reference position mark is an image indicating a position to be a moving target of the pseudo alignment index image (e.g. an image of a parentheses-type), and is always displayed at a predetermined reference position regardless of change of a fixation position of the subject's eye E. The reference position refers to a central position of the observation image in the display 240A. An examiner operates an operation unit 240B to move the optical system for inspection in a three-dimensional manner such that the pseudo alignment index image displayed in a screen of the display 240A enters the inside of the alignment reference position mark, thereby performing alignment of the optical system for inspection with respect to the subject's eye E.

(Image Formation Unit)

An image formation unit 220 forms image data on a tomographic image of the eyeground Ef on the basis of a detection signal from the CCD image sensor 115. This processing includes noise elimination (noise reduction), filter processing, Fast Fourier Transform (FFT), and the like, as with the optical coherence tomography of a conventional spectral domain type. In a case of an OCT device of another type, the image formation unit 220 performs publicly known processing corresponding to the type.

The image formation unit 220 includes the circuit board described above, for example. In the present specification, the "image data" and the "image" based on it may be identified.

(Image Processing Unit)

An image processing unit 230 applies various image processing items and analysis processing to an image formed by the image formation unit 220. For example, the image processing unit 230 performs various correction processing items, such as luminance correction of an image, and dispersion correction. In addition, the image processing unit 230 applies the various image processing items and the analysis processing to an image (e.g. an eyeground image, and an anterior eye image) acquired by the fundus camera unit 2.

The image processing unit 230 performs publicly known image processing, such as interpolation processing of interpolating pixels between tomographic images, to form image data on a three-dimensional image of the eyeground Ef. The image data on a three-dimensional image refers to image data in which a position of a pixel is defined by a three-dimensional coordinate system. The image data on a three-dimensional image includes image data formed of voxels arranged in a three-dimensional manner. The image data is called volume data, voxel data, or the like. When an image based on volume data is displayed, the image processing unit 230 applies rendering processing (e.g. volume rendering, and maximum intensity projection (MIP)) to the volume data to form pseudo image data on a three-dimensional image as viewed from a specific line of sight direction. The display 240A displays the pseudo three-dimensional image.

Stack data on a plurality of tomographic images also can be formed as image data of a three-dimensional image. The stack data is an image data acquired by arranging a plurality of tomographic images acquired along a plurality of scanning lines in a three-dimensional manner on the basis of a positional relationship of the scanning lines. That is, the stack data is an image data acquired by allowing a plurality of tomographic images defined originally by an individual two-dimensional coordinate system to be expressed by one three-dimensional coordinate system (or to be embedded in one three-dimensional space).

(Analysis Unit)

The image processing unit 230 is provided with the analysis unit 231. The analysis unit 231 analyzes two photographed images that are substantially simultaneously acquired by the anterior eye cameras 300A and 300B to acquire a three-dimensional position of the subject's eye E. As an example of a configuration to perform this processing, the analysis unit 231 includes an image correction unit 2311, a feature point identifying unit 2312, and a three-dimensional position calculating unit 2313.

(Image Correction Unit)

The image correction unit 2311 corrects distortion of each of photographed images acquired by the anterior eye camera 300 on the basis of the aberration information stored in the storage unit 212. This processing is performed by using a publicly known image processing art based on a correction coefficient for correcting distortion aberration, for example. If distortion aberration of an optical system of the anterior eye camera 300 to be applied to a photographed image is sufficiently small, for example, it is unnecessary to provide the aberration information and the image correction unit 2311, described above.

(Feature Point Identifying Unit)

The feature point identifying unit 2312 analyzes each of the photographed images, whose distortion aberration is corrected by the image correction unit 2311, to identify a position (referred to as a feature point position) in the photographed image, corresponding to a predetermined feature point of the anterior eye Ea. For example, the center of a pupil or the tip of the cornea of the subject's eye E is applied to the predetermined feature point. Hereinafter, a specific example of processing of identifying the center of a pupil will be described.

First, the feature point identifying unit 2312 identifies an image area (pupil area) corresponding to a pupil of the subject's eye E on the basis of distribution of pixel values (e.g. luminance values) of a photographed image. In general, since a pupil is imaged at brightness lower than other portions, the pupil area can be identified by searching for an image area with low brightness. At this time, the pupil area may be identified in consideration of the shape of the pupil. That is, the feature point identifying unit 2312 can be configured such that the pupil area is identified by searching for an image area in a substantially circular shape as well as with low brightness.

Next, the feature point identifying unit 2312 identifies a center position of the pupil area identified. Since the pupil is in a substantially circular shape as described above, identifying a contour of the pupil area as well as a center position of an approximate ellipse of the contour enables the center position to be set as the center of the pupil. In addition, the center of gravity of the pupil area may be acquired to be set as the center of a pupil.

Even if another feature point is used, a position of the feature point can be identified on the basis of distribution of pixel values of a photographed image, as described above.

(Three-Dimensional Position Calculating Unit)

The three-dimensional position calculating unit 2313 calculates a three-dimensional position of a feature point of the subject's eye E on the basis of a position of each of the two or more anterior eye cameras 300 and a position of the feature point in each of two or more photographed images identified by the feature point identifying unit 2312. This processing will be described with reference to FIGS. 5A and 5B.

Figure 5A:
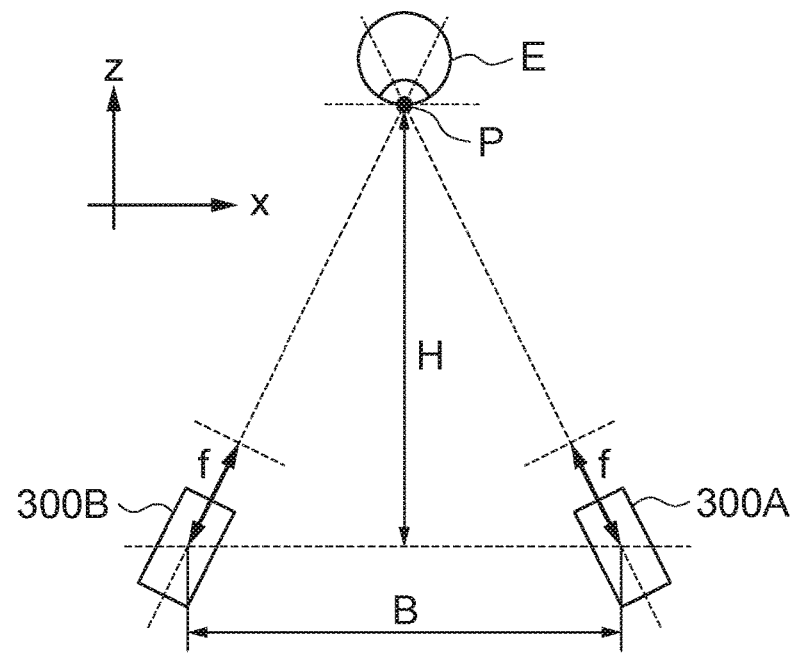
FIG. 5A is a schematic view to describe processing performed in the embodiment of the ophthalmological device according to the present invention.
Figure 5B:
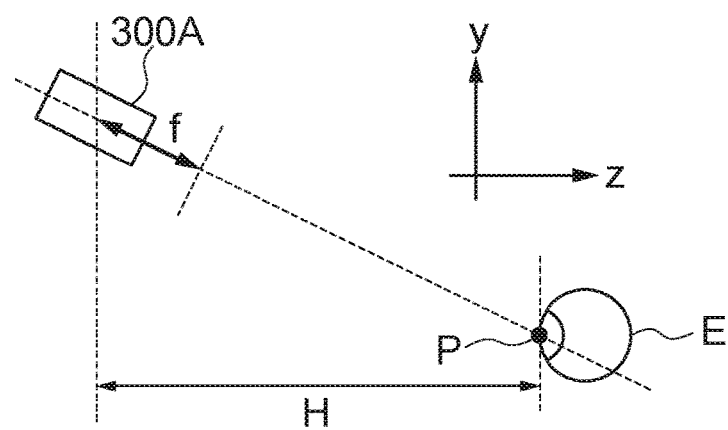
FIG. 5B is a schematic view to describe processing performed in the embodiment of the ophthalmological device according to the present invention.

FIG. 5A is a top view illustrating a positional relationship between the subject's eye E and the anterior eye cameras 300A and 300B. FIG. 5B is a side view illustrating a positional relationship between the subject's eye E and the anterior eye cameras 300A and 300B. A distance (baseline length) between the two anterior eye cameras 300A and 300B is designated by "B". A distance (photographing distance) between a baseline of the two anterior eye cameras 300A and 300B, and a feature point P of the subject's eye E is designated by "H". A distance (screen distance) between each of the anterior eye cameras 300A and 300B, and its screen plane, is designated by "f".

In the placement as described above, resolution of a photographed image acquired by the anterior eye cameras 300A and 300B is expressed by the following expressions, where Δp is pixel resolution.

Resolution in a xy-directions (plane resolution): $\Delta xy = H \times \Delta p/f$ Resolution in the z-direction (depth resolution): $\Delta z = H \times H \times \Delta p/(B \times f)$ The three-dimensional position calculating unit 2313 calculates a three-dimensional position of the feature point P, or a three-dimensional position of the subject's eye E, by applying publicly known trigonometry in consideration of the arrangement relationship illustrated in FIGS. 5A and 5B to a known position of each of the anterior eye cameras 300A and 300B, and a position in each of two photographed images, corresponding to the feature point P.

The three-dimensional position of the subject's eye E calculated by the three-dimensional position calculating unit 2313 is transmitted to the control unit 210.

In this embodiment, the anterior eye cameras 300A and 300B, and the analysis unit 231 are an example of the "subject's eye position acquiring unit". That is, in this embodiment, while the analysis unit 231 analyzes two photographed images that are substantially simultaneously acquired by the anterior eye cameras 300A and 300B to acquire a three-dimensional position of the subject's eye E, an aspect of acquiring the three-dimensional position of the subject's eye E is not limited to this embodiment. For example, the three-dimensional position of the subject's eye E may be acquired from a front face image of the subject's eye E (an observation image of the anterior eye Ea) by using an optical lever method, or the three-dimensional position of the subject's eye E may be acquired from an external device.

The image processing unit 230 serving as described above includes the microprocessor, the RAM, the ROM, the hard disk drive, the circuit board, and the like, described above, for example. A storage device such as the hard disk drive previously stores a computer program for causing the microprocessor to execute the function described above.

(User Interface)

A user interface 240 includes the display 240A, and the operation unit 240B. The display 240A includes a display device of the calculation control unit 200 described above, and the display device 3. The operation unit 240B includes an operation device of the calculation control unit 200 described above. The operation unit 240B may include various buttons and keys, provided in a body or an exterior of the ophthalmological device 1. For example, if the fundus camera unit 2 has a body similar to that of a conventional fundus camera, the operation unit 240B may include a joystick, an operation panel, and the like, provided in the body. In addition, the display 240A may include various display devices, such as a touch panel provided in the body of the fundus camera unit 2.

It is unnecessary that each of the display 240A and the operation unit 240B is configured as an individual device. For example, a device in which a display function and an operation function are integrated like a touch panel also can be used. In that case, the operation unit 240B includes the touch panel, and a computer program. Operation contents for the operation unit 240B are inputted into the control unit 210 as an electric signal. In addition, a graphical user interface (GUI) displayed in the display 240A and the operation unit 240B may be used for operation and information input.

(Operation)

Figure 6:
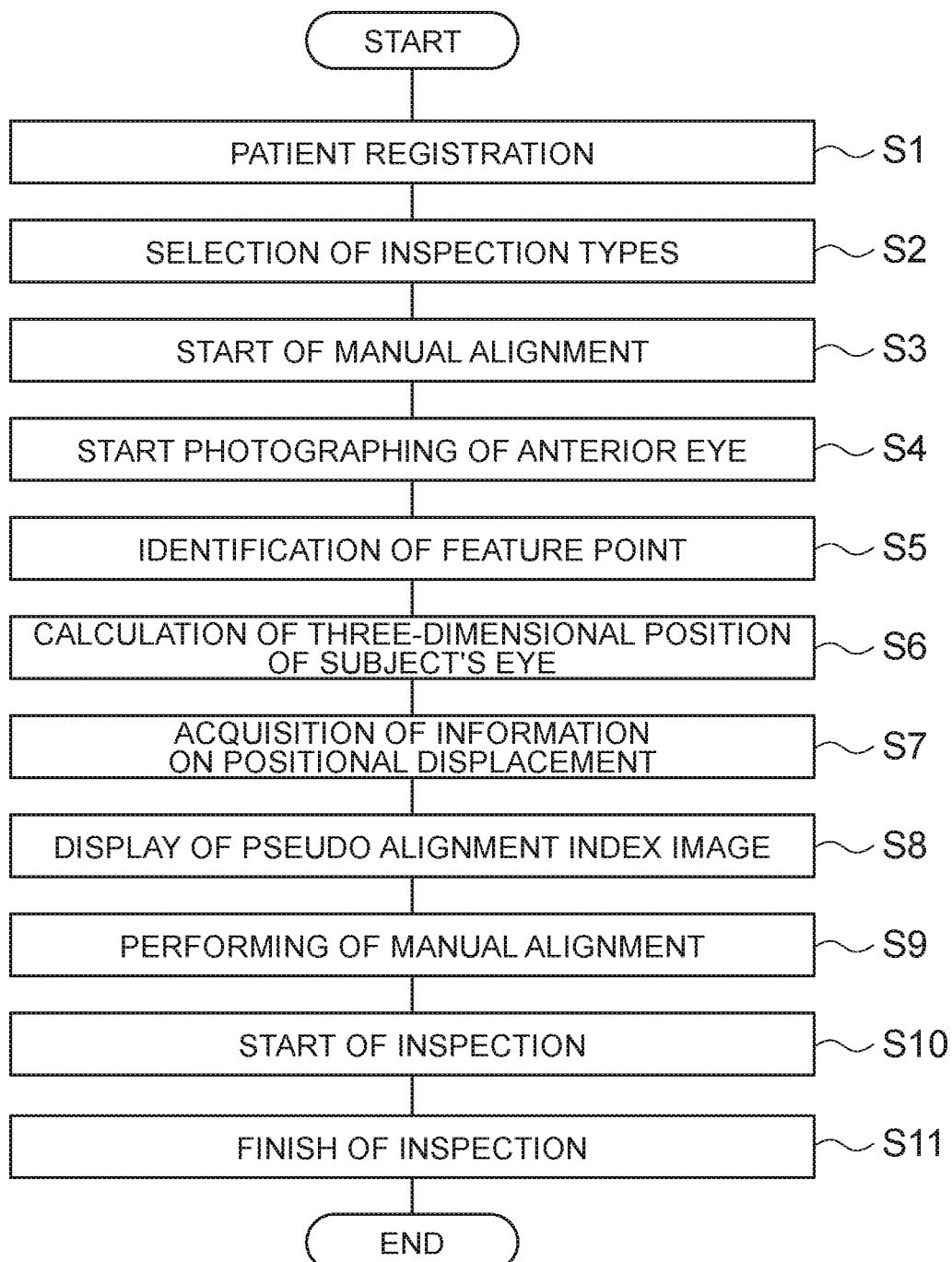
FIG. 6 is a flow chart illustrating an example of operation of the embodiment of the ophthalmological device according to the present invention.

Operation of the ophthalmological device 1 will be described. A flow chart illustrated in FIG. 6 shows an example of the operation of the ophthalmological device 1.

(S1: Patient Registration)

First, a user inputs patient information on a subject by using the user interface 240. The patient information includes a patient ID, a patient name, and the like.

(S2: Selection of Inspection Types)

Next, the user selects and inputs inspection types to be applied to the subject by using the user interface 240. Items of the inspection types include: an inspection portion (e.g. an eyeground central portion, an eyeground peripheral portion, an optic disk, and a macula lutea); a subject's eye (e.g. a left eye, a right eye, both eyes); an image photographing pattern (e.g. only an eyeground image, only an OCT image, and both the images); an OCT scan pattern (e.g. a line scan, a cross scan, a radial scan, a circular scan, and a three-dimensional scan); and the like. In this example of the operation, a peripheral portion of the eyeground Ef is selected as an inspection portion.

(S3: Start of Manual Alignment)

When the selection of inspection types is completed, a start of manual alignment is instructed. The control unit 210 may automatically instruct the start after receiving the selection of inspection types shown in step S2, or the user may manually instruct the start by using the operation unit 240B.

(S4: Start of Photographing of Anterior Eye)

When the start of manual alignment is instructed, the control unit 210 causes each of the anterior eye cameras 300A and 300B to start photographing of the anterior eye Ea. This photographing is photographing of a moving image for the anterior eye Ea. Each of the anterior eye cameras 300A and 300B performs the photographing of a moving image at a predetermined frame rate. Photographing timing of each of the anterior eye cameras 300A and 300B may be synchronized by the control unit 210. Each of the anterior eye cameras 300A and 300B sequentially transmits an acquired frame to the control unit 210 in real time. The control unit 210 associates frames acquired by both the anterior eye cameras 300A and 300B with each other in accordance with the photographing timing. That is, the control unit 210 associates frames that are substantially simultaneously acquired by both the anterior eye cameras 300A and 300B with each other. This association is established on the basis of synchronization control as described above, or on the basis of input timing of the frames from the anterior eye cameras 300A and 300B, for example. The control unit 210 transmits a pair of frames associated with each other to the analysis unit 231.

(S5: Identification of Feature Point)

The image correction unit 2311 corrects distortion of each of the frames transmitted from the control unit 210 on the basis of aberration information stored in the storage unit 212. This correction processing is performed according to the manner described above. The pair of frames in which distortion is corrected is transmitted to the feature point identifying unit 2312.

The feature point identifying unit 2312 analyzes each of the frames transmitted from the image correction unit 2311 to perform processing of identifying a position in each of the frames, corresponding to a feature point (center of a pupil) of the anterior eye Ea.

If identification of the feature point fails, the processing of identifying the feature point can be controlled so as to be performed again after the anterior eye cameras 300A and 300B are moved in a direction away from the support part 440 and/or in an outward direction from the support part 440. Moving the anterior eye cameras 300A and 300B in the direction away from the support part 440 increases a distance between the anterior eye cameras 300A and 300B, and the subject (subject's eye E) to enable a wider range in the subject's face to be photographed. Accordingly, a possibility that the subject's eye E is disposed within a favorably photographable range by the anterior eye cameras 300A and 300B increases. In addition, the anterior eye cameras 300A and 300B are moved toward a subject's ear side by moving the anterior eye cameras 300A and 300B in the outward direction from the support part 440, thereby increasing a possibility that the subject's eye E is disposed within a favorably photographable range. Combination of movements in these two directions further increases a possibility that the subject's eye E is disposed within a favorably photographable range.

It is also possible to determine whether an image corresponding to the anterior eye Ea is positioned within a predetermined area in a frame. If it is determined that the image of the anterior eye Ea is not positioned within the predetermined area, it is possible to perform control of movement of the anterior eye cameras 300A and 300B as described above.

(S6: Calculation of Three-Dimensional Position of Subject's Eye)

The three-dimensional position calculating unit 2313 calculates a three-dimensional position of a feature point (center of a pupil) of the subject's eye E on the basis of a position of each of the anterior eye cameras 300A and 300B, and a position of a feature point of each of the pair of frames identified by the feature point identifying unit 2312. This processing is performed according to the manner described above.

(S7: Acquisition of Information on Positional Displacement)

The control unit 210 acquires information on positional displacement of the optical system for inspection with respect to the subject's eye E on the basis of the three-dimensional position of the feature point (center of a pupil) calculated in step S6. This processing is performed as follows, for example. First, the control unit 210 acquires a current position of the optical system for inspection. The current position is acquired from control history for the optical system driving unit 2A that moves the fundus camera unit 2, for example. In addition, the current position also can be acquired from a detection result acquired by a position sensor that is provided to detect a position of the fundus camera unit 2. A coordinate system defining the three-dimensional position (coordinate) of the subject's eye E acquired in step S6 and a coordinate system defining current position (coordinate) of the optical system for inspection are to be common. Alternatively, coordinate transformation between both the coordinate systems is to be known.

The information on positional displacement indicates displacement (an amount of positional displacement and a positional displacement direction) from a proper position of the optical system for inspection with respect to the subject's eye E. The proper position is a target position of favorable alignment of the optical system for inspection to inspect the subject's eye E, wherein an axis of the subject's eye E and an optical axis of the optical system for inspection coincide with each other in the x-direction (side-to-side direction) and the y-direction (vertical direction), and the proper position is away from the subject's eye E in the z-direction (fore-and-aft direction, or optical axis direction) by a predetermined operation distance. Since the operation distance is known and the three-dimensional position of the subject's eye E is acquired in step S6, it is easy to acquire a coordinate of the target position of alignment in the common coordinate system described above, for example.

(S8: Display of Pseudo Alignment Index Image)

The control unit 210 causes each of the pseudo alignment index image and the alignment reference position mark to be displayed at a predetermined position in a screen of the display 240A while superimposing them on an observation image to form a composite display on the basis of information on positional displacement acquired in step S8. A display example of the pseudo alignment index image and the alignment reference position mark will be described below.

First Display Example

Figure 7A:
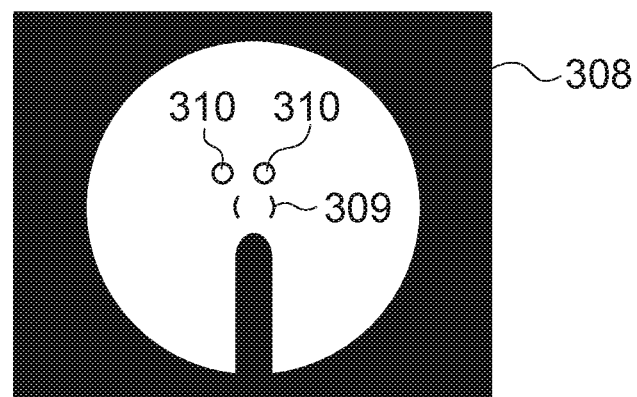
FIG. 7A is a schematic view illustrating an example of a display screen in the embodiment of the ophthalmological device according to the present invention.
Figure 7B:
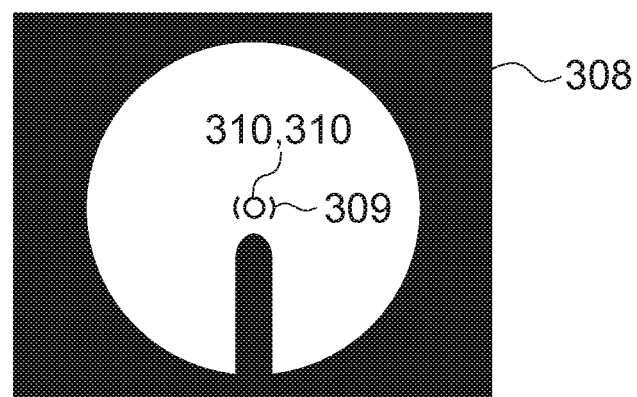
FIG. 7B is a schematic view illustrating an example of a display screen in the embodiment of the ophthalmological device according to the present invention.

With reference to FIGS. 7A and 7B, a first display example will be described. FIGS. 7A and 7B each illustrate an example of a display screen to be used for alignment adjustment. This display screen corresponds to a screen displayed in the display 240A. While there is no illustration, an observation image (an eyeground image of the subject's eye E) acquired by the fundus camera unit 2 is displayed in the display screen illustrated in FIGS. 7A and 7B.

In FIGS. 7A and 7B, an alignment reference position mark (parentheses mark) 309 is displayed at a reference position in a display screen 308. The reference position refers to a central position of the observation image. The alignment reference position mark 309 is an image showing a position of a moving target of pseudo alignment index images 310. The display screen 308 displays the two pseudo alignment index images 310 and 310. A display position of each of the two pseudo alignment index images 310 and 310 changes in accordance with information on positional displacement of the optical system for inspection with respect to the subject's eye E. That is, the control unit 210 controls the display position of each of the two pseudo alignment index images 310 and 310 in accordance with displacement (an amount and direction of positional displacement) of the optical system for inspection with respect to the subject's eye E in each of the x-direction (side-to-side direction), the y-direction (vertical direction), and the z-direction (direction of working distance).

For example, if the optical system for inspection is displaced in the xy-directions with respect to the subject's eye E, the pseudo alignment index image 310 is displayed at a position away from the alignment reference position mark 309, as illustrated in FIG. 7A. In addition, if the optical system for inspection is displaced in the z-direction with respect to the subject's eye E, each of the two pseudo alignment index images 310 and 310 is displayed away from each other at a predetermined interval, as illustrated in FIG. 7A. Meanwhile, if alignment in all the xyz-directions is proper, the pseudo alignment index images 310 and 310 are displayed inside the alignment reference position mark 309 while superimposed with each other, as illustrated in FIG. 7B.

That is, a display position of each of the pseudo alignment index images 310 and 310 with respect to the alignment reference position mark 309 is controlled so as to change in accordance with displacement of the optical system for inspection in the xy-directions with respect to the subject's eye E (an amount and a direction of positional displacement in the xy-directions from a proper position). In addition, an interval (distance) between the pseudo alignment index images 310 and 310 is controlled so as to be displayed while changing in accordance with displacement of the optical system for inspection in the z-direction with respect to the subject's eye E (an amount of positional displacement in the z-direction from the proper position).

According to the first display example described above, alignment adjustment can be manually performed while an observation image (an eyeground image of the subject's eye E) displayed in a screen of the display 240A is observed with a familiar operational feeling.

In this embodiment, since the pseudo alignment index image is displayed in a pseudo manner, the alignment reference position mark can be always displayed at a predetermined reference position regardless of change of an inspection portion (or a projection position of a fixation target). Accordingly, even if an eyeground peripheral portion is selected as an inspection portion, for example, there is less possibility that an alignment index image disappears in a screen of a display, as compared with a conventional ophthalmological device, and thus alignment adjustment can be smoothly performed on the basis of quantitative information without depending on experience and proficiency of a user.

Second Display Example

Figure 8A:
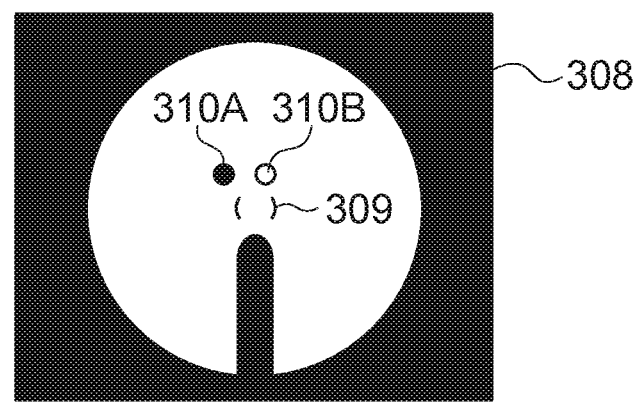
FIG. 8A is a schematic view illustrating an example of a display screen in the embodiment of the ophthalmological device according to the present invention.
Figure 8B:
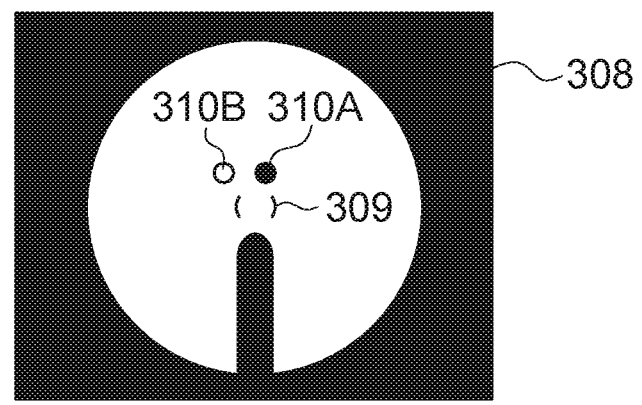
FIG. 8B is a schematic view illustrating an example of a display screen in the embodiment of the ophthalmological device according to the present invention.

With reference to FIGS. 8A and 8B, a second display example will be described. FIGS. 8A and 8B illustrate examples of display screens in which position (alignment) of the optical system for inspection with respect to the subject's eye E in the z-direction is displaced forward and rearward, respectively. In the present specification, a direction toward a subject side is indicated as a forward direction, and an opposite direction thereto is indicated as a rearward direction.

In the second display example, as shown in FIGS. 8A and 8B, the control unit 210 causes two pseudo alignment index images 310A and 310B to be displayed such that the first pseudo alignment index image 310A is displayed in a first color (illustrated by a solid circle) and the second pseudo alignment index image 310B is displayed in a second color different from the first color (illustrated by an open circle).

If positional displacement in the z-direction is the forward direction, the control unit 210 causes the first pseudo alignment index image 310A to be displayed on the left side as well as the second pseudo alignment index image 310B to be displayed on the right side, as illustrated in FIG. 8A. On the other hand, if the positional displacement in the z-direction is the rearward direction, the control unit 210 causes the first pseudo alignment index image 310A to be displayed on the right side as well as the second pseudo alignment index image 310B to be displayed on the left side, as illustrated in FIG. 8B. As with the first display example, an interval (distance) between the two pseudo alignment index images 310A and 310B changes in accordance with an amount of positional displacement in the z-direction (direction of working distance).

In the second display example described above, the two alignment index images are displayed in display modes different from each other, and display positions of the two alignment index images change places depending on whether positional displacement in the z-direction of the optical system for inspection with respect to the subject's eye E is the forward direction or the backward direction. Accordingly, it is possible to intuitively grasp not only an amount of positional displacement in the z-direction, but also whether the positional displacement in the z-direction is the forward direction or the rearward direction, from a positional relationship between the two pseudo alignment index images 310A and 310B.

In the first display example described above, two alignment index images are displayed in the same display mode, and thus it is difficult to intuitively grasp a direction of positional displacement in the z-direction from a positional relationship between the two pseudo alignment index images 310A and 310B.

In the second display example, a form of changing a display mode of each of the two pseudo alignment index images 310A and 310B is not limited to the example described above, and thus other than color, for example, size, shape, or blinking pattern, may be changed, and a combination thereof may be available. In addition, any visually discriminable form, such as pattern, brightness, density, and transparency, is available.

Figure 9:
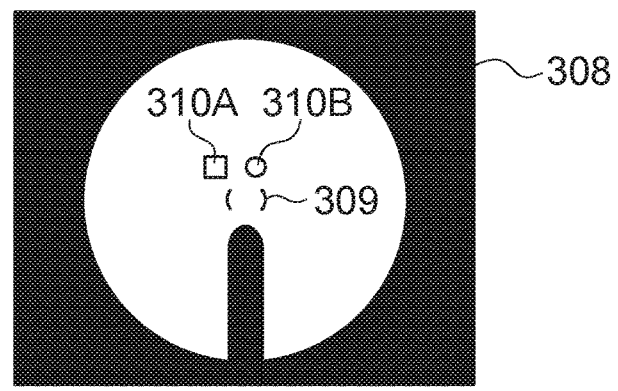
FIG. 9 is a schematic view illustrating an example of a display screen in the embodiment of the ophthalmological device according to the present invention.
Figure 10:
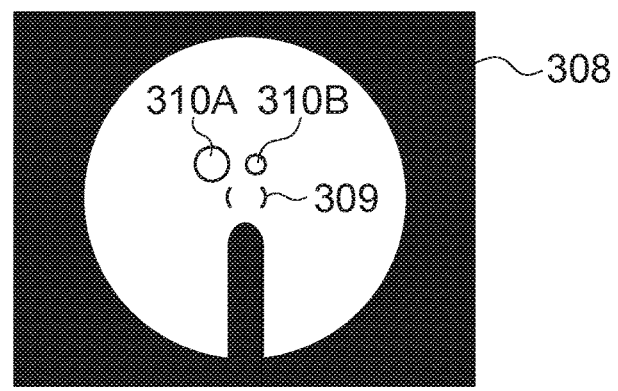
FIG. 10 is a schematic view illustrating an example of a display screen in the embodiment of the ophthalmological device according to the present invention.
Figure 11:
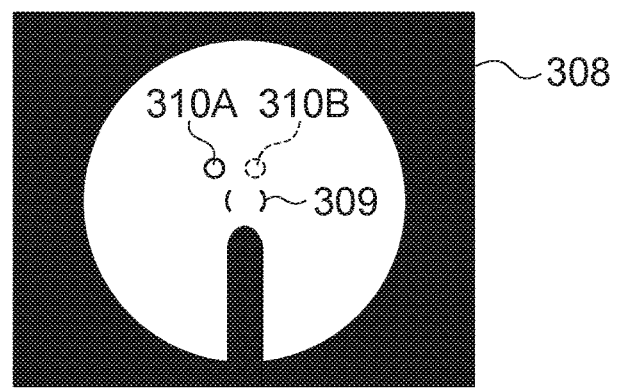
FIG. 11 is a schematic view illustrating an example of a display screen in the embodiment of the ophthalmological device according to the present invention.

Variations of the second display example will be described with reference to FIGS. 9 to 11. FIGS. 9 to 11 each illustrate a case where positional displacement in the z-direction is in the forward direction, and if the positional displacement in the z-direction is in the rearward direction, the two pseudo alignment index images 310A and 310B are displayed while their display positions are exchanged from each other.

(First Variation)

A first variation is configured so that the two pseudo alignment index images 310A and 310B are different from each other in shape. That is, in the two pseudo alignment index images 310A and 310B, the first pseudo alignment index image 310A is displayed by a quadrangular mark and the second pseudo alignment index image 310B is displayed by a circular mark, as illustrated in FIG. 9.

(Second Variation)

A second variation is configured so that the two pseudo alignment index images 310A and 310B are different from each other in size. For example, in the two pseudo alignment index images 310A and 310B, a large size of the first pseudo alignment index image 310A is displayed and a small size of the second pseudo alignment index image 310B is displayed, as illustrated in FIG. 10.

(Third Variation)

A third variation is configured so that the two pseudo alignment index images 310A and 310B are different from each other in blinking pattern. For example, in the two pseudo alignment index images 310A and 310B, the first pseudo alignment index image is always displayed (displayed by a solid line) and the second pseudo alignment index image is displayed in a blinking manner (displayed by a dashed line), as illustrated in FIG. 11.

Third Display Example

Figure 12A:
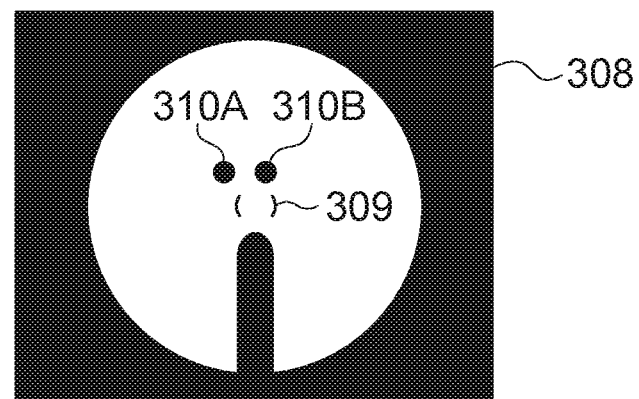
FIG. 12A is a schematic view illustrating an example of a display screen in the embodiment of the ophthalmological device according to the present invention.
Figure 12B:
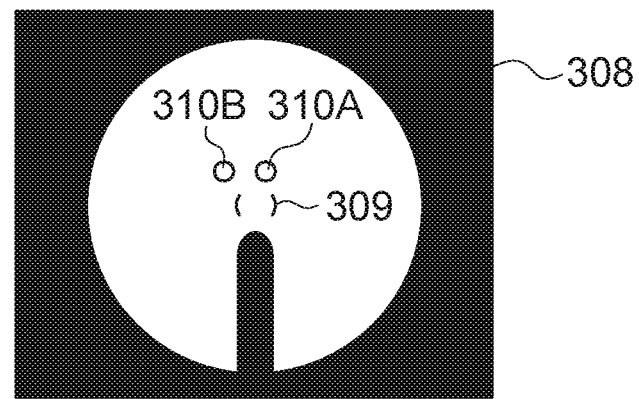
FIG. 12B is a schematic view illustrating an example of a display screen in the embodiment of the ophthalmological device according to the present invention.

With reference to FIGS. 12A and 12B, a third display example will be described.

FIGS. 12A and 12B illustrate examples of display screens in which positional displacement of the optical system for inspection with respect to the subject's eye E in the z-direction is forward and rearward directions, respectively. As illustrated in FIG. 12A, if the positional displacement in the z-direction is in the forward direction, the control unit 210 causes the two pseudo alignment index images 310A and 310B to be displayed in a first color (illustrated by a solid circle). On the other hand, as illustrated in FIG. 12B, if the positional displacement in the z-direction is in the rearward direction, the control unit 210 causes the two pseudo alignment index images 310A and 310B to be displayed in a second color (illustrated by an open circle) different from the first color.

In the third display example as described above, as with the first display example, while the two pseudo alignment index images 310A and 310B are displayed in the same display mode, a display form of each of the two pseudo alignment index images 310A and 310B is to be different from each other depending on whether positional displacement in the z-direction (direction of working distance) is in the forward direction or in the rearward direction. Accordingly, it is possible to intuitively grasp whether the positional displacement in the z-direction is in the forward direction or the rearward direction, from the display form of each of the two pseudo alignment index images 310A and 310B, thereby enabling a user to smoothly perform alignment adjustment without doubt.

In the third display example, a form of changing a display mode of each of the two pseudo alignment index images 310A and 310B is not limited to the example described above, and thus, as with the second display example, other than color, for example, size, shape, or blinking pattern, may be changed, and a combination thereof may be available. In addition, any visually discriminable form, such as pattern, brightness, density, and transparency, is available.

(S9: Performing of Manual Alignment)

A user performs predetermined operation using the operation unit 240B to move the optical system for inspection while observing the observation image displayed and checking the pseudo alignment index image.

At this time, the control unit 210 enables a display position of the pseudo alignment index image to be changed in accordance with contents of movement of the optical system for inspection. For example, the control unit 210 acquires information on positional displacement in real time again in accordance with the contents of movement of the optical system for inspection to update a display of the pseudo alignment index image in real time in accordance with the newly-acquired information on positional displacement.

In addition, the control unit 210 determines whether positional displacement in all the xyz-directions of the optical system for inspection with respect to the subject's eye E is within a predetermined allowable range or not. If it is determined that the positional displacement is within the allowable range, a pseudo alignment index image may be displayed in a display mode different from that in a case where the positional displacement is out of the allowable range. For example, in the second display example described above, if positional displacement is out of the allowable range, the two pseudo alignment index images 310A and 310B are displayed in the first and second colors, respectively. On the other hand, if the positional displacement is within the allowable range, the two pseudo alignment index images 310A and 310B are displayed in a third color different from the first and second colors.

A form of changing a display mode of each of the two pseudo alignment index images when it is determined that the positional displacement is within the allowable range, is not limited to the example described above, and thus other than color, for example, size, shape, or blinking pattern, may be changed, and a combination thereof may be available. In addition, any visually discriminable form, such as pattern, brightness, density, and transparency, is available.

Referring to information on the subject's eye enables correctness of manual alignment to be further improved. The information on the subject's eye is measurement information showing characteristics of the subject's eye, acquired by an inspection previously performed with respect to the subject's eye E, for example. The measurement information may be acquired by the ophthalmological device or another ophthalmological device. Then, the measurement information is previously stored in the storage unit 212 by being associated with a patient ID, for example.

The control unit 210 selects the measurement information corresponding to the subject's eye E on the basis of the patient ID, and the like. In addition, the control unit 210 creates information on positional displacement on the basis of the selected measurement information and the three-dimensional position of the subject's eye E acquired by the analysis unit 231. An example of this processing enables information on positional displacement (amount and direction of positional displacement) in the x-direction and the y-direction to be corrected on the basis of a deviation of a cornea shape. In addition, it is possible to correct information on positional displacement (amount and direction of positional displacement) in the z-direction on the basis of eye axial length. The latter is particularly effective when an eyeground is inspected.

As described above, information on positional displacement with higher correctness in accordance with an individual difference in a subject's eye can be acquired and presented by creating information on positional displacement in consideration of the measurement information of the subject's eye E.

(S10: Start of Inspection)

When the processing of manual alignment in step S9 is finished, the control unit 210 starts an inspection designated in step S2.

(S11: Finish of Inspection)

When the inspection of the subject's eye E is finished, this example of operation is finished.

While an operation example in a case where a peripheral portion of an eyeground Ef is selected as an inspection portion is described in the description above, in a case where a central portion of an eyeground is selected as an inspection portion, a pseudo alignment index image is displayed with reference to a reference position (a central position of an observation image) where an alignment reference position mark is to be displayed, as with the operation example described above.

(Function and Effect)

Function and effect of the ophthalmological device 1 as described above will be described.

The ophthalmological device 1 includes the optical system for inspection, the display 240A, the two anterior eye cameras 300A and 300B (photographing unit), the analysis unit 231, and the control unit 210. The optical system for inspection is an optical system for inspecting a subject's eye E, and includes the photographic optical system 30 for photographing an eyeground of the subject's eye E. The two anterior eye cameras 300A and 300B substantially simultaneously photograph an anterior eye Ea of the subject's eye E from different directions. The analysis unit 231 analyzes a photographed image acquired by the anterior eye camera 300 to acquire a three-dimensional position of the subject's eye E. The control unit 210 acquires information on positional displacement of the optical system for inspection with respect to the subject's eye on the basis of the three-dimensional position of the subject's eye E, acquired by the analysis unit 231, to cause two pseudo alignment index images whose positions vary with respect to a reference position of alignment preset in a display 240A to be displayed in a screen of the display 240A in a pseudo manner in accordance with the information on positional displacement.

The ophthalmological device 1 described above acquires information on positional displacement from a proper position of the optical system for inspection with respect to the subject's eye E on the basis of a three-dimensional position of the subject's eye E calculated from photographed images acquired by the anterior eye cameras 300A and 300B, and displays a pseudo alignment index image in a screen of a display in a pseudo manner in accordance with the acquired information on positional displacement. That is, the pseudo alignment index image created in a pseudo manner by the control unit 210 is displayed in the screen of the display 240A instead of an alignment index image (optical alignment index image) projected on the subject's eye E by an alignment optical system. Thus, it is possible to always set a reference position of alignment preset in the screen of the display at a predetermined position regardless of an inspection portion (or a fixation position of the subject's eye E). Accordingly, even if an eyeground peripheral portion is selected as an inspection portion, for example, there is less possibility that an alignment index image disappears in a screen of a display, as compared with a conventional ophthalmological device, and thus alignment adjustment can be smoothly performed on the basis of quantitative information without depending on experience and proficiency of a user. Thus, it is possible to smoothly and easily perform alignment adjustment of the optical system for inspection with respect to a subject's eye by hand with a familiar operational feeling.

Since the ophthalmological device 1 of this embodiment is capable of manually performing alignment adjustment without providing an alignment optical system that projects an alignment index on the subject's eye E, the device can be reduced in size, and can be reduced in the number of components for cost reduction and improvement in maintenance as compared with a device including the alignment optical system.

Modification

The configurations each described above are only an example of suitably practicing the present invention. Thus, any modification (e.g. elimination, replacement, and addition) within the scope of the present invention can be appropriately applied.

The anterior eye camera 300 (photographing unit) can be disposed below (−y-direction) a lens center of the objective lens 22. Accordingly, it is possible to reduce a possibility that an eyelid or eyelashes of a subject is displayed in a photographed image acquired by the anterior eye camera 300 (photographing unit). Thus, even if a subject has a deep hollow of an eye (orbit), photographing of an anterior eye can be suitably performed.

In the embodiment described above, two photographed images that are substantially simultaneously acquired by the anterior eye cameras 300A and 300B are combined by the image processing unit 230 so that the composite image can be displayed. This enables a three-dimensional form of the anterior eye Ea to be observed. In addition, the analysis processing of the embodiment described above also can be performed by using the composite image.

In the embodiment described above, the control unit 210 is capable of causing at least one of two photographed images that are substantially simultaneously acquired by the anterior eye cameras 300A and 300B to be displayed. This enables a form of the anterior eye Ea to be observed from different visual points (photographing positions).

The anterior eye camera 300 may be attached to a front face of the body 420, or stored in the body 420. That is, the anterior eye camera 300 may be disposed so as to project from the front face of the body 420, or may be disposed so as to be substantially in flush with the front face of the body 420. The anterior eye camera 300 can be also provided such that its front face is disposed at a position recessed from the front face of the body 420.

In a case where the anterior eye camera 300A is provided so as not to project from the front face of the body 420, there can be acquired advantages such as: eyelid opening as well as external fixation operation is not obstructed; and failure of acquiring positional information due to vignetting of an image itself can be avoided.

The anterior eye camera 300 can be also provided at a position other than the front face of the body 420. For example, while the anterior eye camera 300 is provided at a position in a side face of the body 420, there can be provided an optical system (such as a mirror) that changes a direction of an optical axis of the anterior eye camera 300 to guide light into the subject's eye E. In addition, while the anterior eye camera 300 is provided in the body 420, an optical system similar to the above also can be provided. When the optical system as described above is provided, it is perceived that it is desirable to provide the anterior eye camera 300 and the optical system in the body 420 in consideration of disturbance with respect to photographing of an anterior eye. In that case, it is perceived that it is desirable to use a configuration in which the anterior eye camera 300 and an optical system are separated from another optical system to avoid influence on photographing of an anterior eye by another optical system (e.g. an optical system for inspection). To separate the optical system, an optical path separating member such as a prism and a dichroic mirror can be used.

In the embodiment described above, while a difference in length between an optical path of the signal light LS and an optical path of the reference light LR is changed by changing a position of the optical path length changing unit 41, a method of changing the difference in the optical path length is not limited to this. For example, the difference in the optical path length can be changed by disposing a reflection mirror (reference mirror) in an optical path of reference light so that the reference mirror is moved in a direction of travel of the reference light to change optical path length of the reference light. In addition, the difference in the optical path length may be changed by moving the fundus camera unit 2 and the OCT unit 100 with respect to the subject's eye E to change optical path length of the signal light LS.

A computer program for achieving the embodiment described above can be stored in any recording medium readable by a computer. For this recording medium, a semiconductor memory, an optical disk, a magneto-optical disk (e.g. a CD-ROM, a DVD-RAM, a DVD-ROM, and an MO), a magnetism recording medium (such as a hard disk, a floppy (registered trademark) disk, and a ZIP), can be used, for example.

This program can be also transmitted and received through a network such as the Internet, and a LAN.

The invention claimed is:

1. An ophthalmological device comprising:
an optical system for inspection including a photographic optical system for photographing an eyeground of a subject's eye;
a display that displays an eyeground image of the subject's eye acquired by the photographic optical system;
a subject's eye position acquiring unit that acquires a three-dimensional position of the subject's eye; and
a control unit that acquires information on positional displacement of the optical system for inspection with respect to the subject's eye on the basis of the three-dimensional position to cause a screen of the display to display two alignment index images to be varied in position with respect to a reference position of alignment preset in the display in a pseudo manner, in accordance with the information on positional displacement.

2. The ophthalmological device according to claim 1, wherein
the control unit causes the two alignment index images to be displayed at the reference position of alignment when the optical system for inspection is at a proper position with respect to the subject's eye.

3. The ophthalmological device according to claim 2, wherein
the information on positional displacement includes an amount of positional displacement and a direction of positional displacement in an optical axis direction of the optical system for inspection, and
the control unit changes a distance between the two alignment index images in accordance with the amount of positional displacement as well as changes a display mode of the two alignment index images in accordance with the direction of positional displacement.

4. The ophthalmological device according to claim 3, wherein
the control unit changes at least one display mode among color, shape, size, blinking pattern, pattern, brightness, density, and transparency, of the two alignment index images, in accordance with the direction of positional displacement.

5. The ophthalmological device according to claim 4, further comprising:
a fixation optical system for fixing the subject's eye,
wherein the control units causes an alignment reference position mark to be always displayed at a predetermined reference position regardless of change in a fixation position of the subject's eye by the fixation optical system.

6. The ophthalmological device according to claim 4, wherein
the subject's eye position acquiring unit includes,
two or more photographing units each of which substantially simultaneously photographs an anterior eye of the subject's eye from a different direction, and
an analysis unit that analyzes photographed images acquired by the two or more photographing units to acquire a three-dimensional position of the subject's eye.

7. The ophthalmological device according to claim 3, further comprising:
a fixation optical system for fixing the subject's eye,
wherein the control units causes an alignment reference position mark to be always displayed at a predetermined reference position regardless of change in a fixation position of the subject's eye by the fixation optical system.

8. The ophthalmological device according to claim 3, wherein
the subject's eye position acquiring unit includes,
two or more photographing units each of which substantially simultaneously photographs an anterior eye of the subject's eye from a different direction, and
an analysis unit that analyzes photographed images acquired by the two or more photographing units to acquire a three-dimensional position of the subject's eye.

9. The ophthalmological device according to claim 2, further comprising:
a fixation optical system for fixing the subject's eye,
wherein the control units causes an alignment reference position mark to be always displayed at a predetermined reference position regardless of change in a fixation position of the subject's eye by the fixation optical system.

10. The ophthalmological device according to claim 9, wherein
the subject's eye position acquiring unit includes,
two or more photographing units each of which substantially simultaneously photographs an anterior eye of the subject's eye from a different direction, and
an analysis unit that analyzes photographed images acquired by the two or more photographing units to acquire a three-dimensional position of the subject's eye.

11. The ophthalmological device according to claim 2, wherein
the subject's eye position acquiring unit includes,
two or more photographing units each of which substantially simultaneously photographs an anterior eye of the subject's eye from a different direction, and
an analysis unit that analyzes photographed images acquired by the two or more photographing units to acquire a three-dimensional position of the subject's eye.

12. The ophthalmological device according to claim 1, wherein
the information on positional displacement includes an amount of positional displacement and a direction of positional displacement in an optical axis direction of the optical system for inspection, and
the control unit changes a distance between the two alignment index images in accordance with the amount of positional displacement as well as changes a display mode of the two alignment index images in accordance with the direction of positional displacement.

13. The ophthalmological device according to claim 12, wherein
the control unit changes at least one display mode among color, shape, size, blinking pattern, pattern, brightness, density, and transparency, of the two alignment index images, in accordance with the direction of positional displacement.

14. The ophthalmological device according to claim 13, further comprising:
a fixation optical system for fixing the subject's eye,
wherein the control units causes an alignment reference position mark to be always displayed at a predetermined reference position regardless of change in a fixation position of the subject's eye by the fixation optical system.

15. The ophthalmological device according to claim 13, wherein
the subject's eye position acquiring unit includes,
two or more photographing units each of which substantially simultaneously photographs an anterior eye of the subject's eye from a different direction, and
an analysis unit that analyzes photographed images acquired by the two or more photographing units to acquire a three-dimensional position of the subject's eye.

16. The ophthalmological device according to claim 12, further comprising:
a fixation optical system for fixing the subject's eye,
wherein the control units causes an alignment reference position mark to be always displayed at a predetermined reference position regardless of change in a fixation position of the subject's eye by the fixation optical system.

17. The ophthalmological device according to claim 12, wherein
the subject's eye position acquiring unit includes,
two or more photographing units each of which substantially simultaneously photographs an anterior eye of the subject's eye from a different direction, and
an analysis unit that analyzes photographed images acquired by the two or more photographing units to acquire a three-dimensional position of the subject's eye.

18. The ophthalmological device according to claim 1, further comprising:
a fixation optical system for fixing the subject's eye,
wherein the control units causes an alignment reference position mark to be always displayed at a predetermined reference position regardless of change in a fixation position of the subject's eye by the fixation optical system.

19. The ophthalmological device according to claim 18, wherein
the subject's eye position acquiring unit includes,
two or more photographing units each of which substantially simultaneously photographs an anterior eye of the subject's eye from a different direction, and
an analysis unit that analyzes photographed images acquired by the two or more photographing units to acquire a three-dimensional position of the subject's eye.

20. The ophthalmological device according to claim 1, wherein
the subject's eye position acquiring unit includes,
two or more photographing units each of which substantially simultaneously photographs an anterior eye of the subject's eye from a different direction, and
an analysis unit that analyzes photographed images acquired by the two or more photographing units to acquire a three-dimensional position of the subject's eye.

* * * * *